US010514719B2

(12) United States Patent
Govari et al.

(10) Patent No.: US 10,514,719 B2
(45) Date of Patent: Dec. 24, 2019

(54) SYSTEM AND METHOD FOR SYNCHRONIZATION AMONG CLOCKS IN A WIRELESS SYSTEM

(71) Applicant: Biosense Webster (Israel) Ltd., Yokneam (IL)

(72) Inventors: Assaf Govari, Haifa (IL); Yaron Ephrath, Karkur (IL); Vadim Gliner, Haifa (IL)

( * ) Notice: Subject to any disclaimer, the term of this patent is extended or adjusted under 35 U.S.C. 154(b) by 135 days.

(21) Appl. No.: 15/634,220

(22) Filed: Jun. 27, 2017

(65) Prior Publication Data

US 2018/0373288 A1 Dec. 27, 2018

(51) Int. Cl.
| | |
|---|---|
| G06F 1/12 | (2006.01) |
| G04R 40/06 | (2013.01) |
| G06F 1/14 | (2006.01) |
| G06N 20/00 | (2019.01) |
| G01S 5/16 | (2006.01) |
| G06F 1/10 | (2006.01) |
| A61B 5/06 | (2006.01) |

(52) U.S. Cl.
CPC .................. *G06F 1/12* (2013.01); *G01S 5/16* (2013.01); *G04R 40/06* (2013.01); *G06F 1/10* (2013.01); *G06F 1/14* (2013.01); *G06N 20/00* (2019.01); *A61B 5/062* (2013.01)

(58) Field of Classification Search
CPC ..... G06F 1/10; G06F 1/12; G06F 1/14; G04R 40/06; G06N 20/00
See application file for complete search history.

(56) References Cited

U.S. PATENT DOCUMENTS

| | | |
|---|---|---|
| 4,817,142 A | 3/1989 | Rassel |
| 5,391,199 A | 2/1995 | Ben-Haim |
| 5,712,867 A | 1/1998 | Yokev et al. |
| 6,194,970 B1 | 2/2001 | Nielsen et al. |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2005/0120258 A1 | 6/2005 | Sohda |

(Continued)

FOREIGN PATENT DOCUMENTS

| | | |
|---|---|---|
| WO | 96/05768 A1 | 2/1996 |
| WO | 2009/135160 A2 | 11/2009 |

OTHER PUBLICATIONS

Extended European Search Report dated Dec. 3, 2018 for the European Patent Application No. 18179953.7.

*Primary Examiner* — Fahmida Rahman

(57) ABSTRACT

A system and method for synchronization among clocks within a wireless system is presented. The method can comprise sending a gong signal comprising a gong signal time to the clocks when a fixed amount of time elapses; at each clock, when the gong signal is received and when the gong signal time is not equal to the clock time, setting the clock time to the gong signal time; and at each clock, when the gong signal is not received, setting the clock time to an estimated time; and learning a skew. In one aspect, a Gaussian distribution fitting technique is used for learning and for calculating the estimated time.

16 Claims, 3 Drawing Sheets

(56) References Cited

U.S. PATENT DOCUMENTS

| | | |
|---|---|---|
| 2008/0137563 A1 | 6/2008 | Wang |
| 2011/0276648 A1* | 11/2011 | Soldan ............... G06F 1/12 709/208 |
| 2012/0179415 A1 | 7/2012 | Nara |
| 2013/0272180 A1 | 10/2013 | Hiremath et al. |
| 2014/0064303 A1* | 3/2014 | Aweya ............ H04J 3/0667 370/509 |

* cited by examiner

| CLOCK1 TIME | CLOCK2 TIME | GONG SIGNAL RECEIVED? | CLOCK2 SYNCED TIME |
|---|---|---|---|
| 1:00 | 1:05 | YES | 1:00 |
| 2:00 | 2:05 | YES | 2:00 |
| 3:00 | 3:05 | NO | 3:05 |
| 3:05 | 3:10 | NO | 3:05 |

SYSTEM AND METHOD FOR SYNCHRONIZATION AMONG CLOCKS IN A WIRELESS SYSTEM

SUMMARY

A system synchronizes a plurality of clocks within a wireless system, even when clock signals are not received.

A method for synchronization a plurality of clocks within a wireless system is presented. The method comprises sending a gong signal comprising a gong signal time to the clocks when a fixed amount of time elapses. At each clock, when the gong signal is received and when the gong signal time is not equal to the clock time, the clock time is set to the gong signal time. At each clock, when the gong signal is not received, setting clock time is set to to an estimated time and a skew is learned.

In one embodiment, learning a skew comprises calculating an average difference between the clock time and the gong signal time. In one embodiment, learning a skew comprises calculating mean and standard deviation using the received gong signal and the clock time, and using the calculated mean and standard deviation to determine the estimated time. In one embodiment, the estimated time is determined using the skew and the clock time. In one embodiment, the estimated time is calculated using Gaussian distribution fitting. In one embodiment, the fixed amount of time is one millisecond.

A computer program product for synchronization among clocks within a wireless system, even when clock signals are not received, is also presented.

BRIEF DESCRIPTION OF THE DRAWINGS

A more detailed understanding can be had from the following description, given by way of example in conjunction with the accompanying drawings wherein.

DETAILED DESCRIPTION

Figures 1, 2:
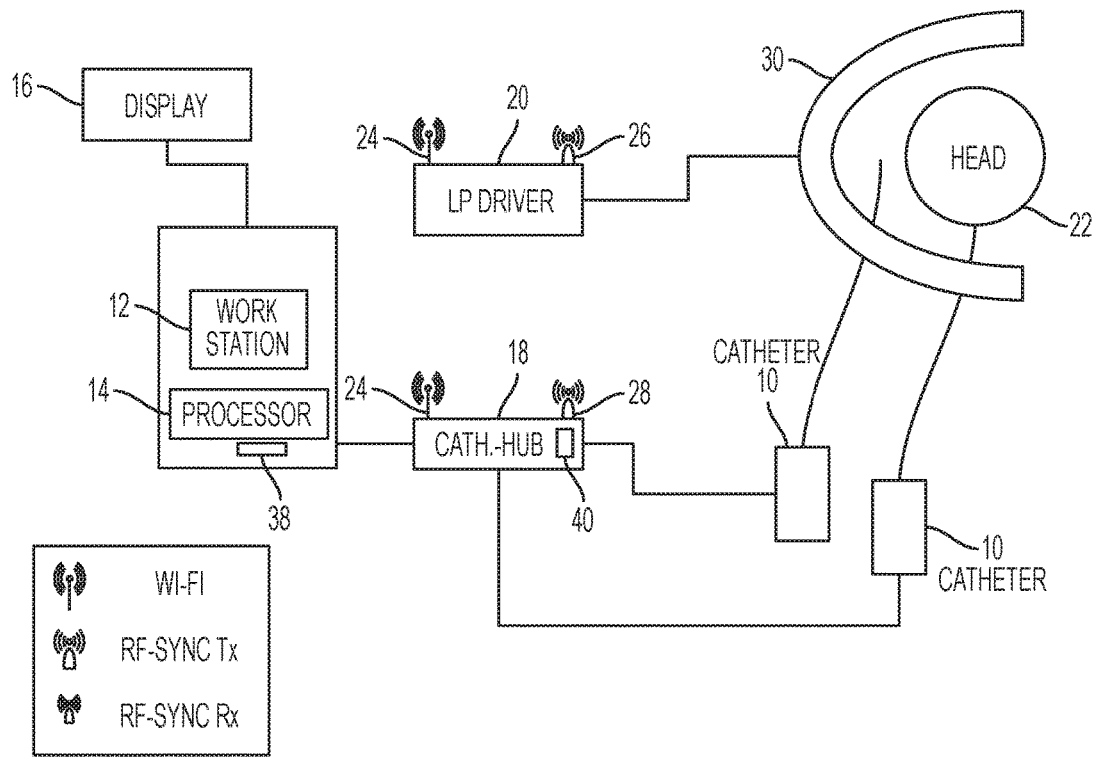
FIG. 1 is a schematic overview of the system in accordance with an embodiment of the present invention.
FIG. 2 is a schematic overview of a method for synchronization between clocks in a wireless system, in accordance with an embodiment of the present invention.

The proposed system is directed to the problem of wireless systems and the potential loss of synchronization among clocks in the wireless system due to missing clock signals. A system and method is needed that compensates for the failure of a clock within a wireless system to pick up a clock signal. The system would provide for synchronization between/among clocks in the wireless system, even when one or more gong or "re-set clock" signals are not received.

Magnetic navigation systems used for navigating tools, such as medical implements, catheters, wireless devices, etc., generally comprise coils with magnetic fields, and each coil has its own frequency. For example, a location field generated by the field generators of the location pad can emit fifteen frequencies. Additionally, the magnetic navigation systems include one or more sensors in space, each sensor typically receiving all coil frequencies. Since each coil has a unique frequency with respect to other coils, the sensor is able to determine the location of each coil.

One such magnetic navigation system can be found in the CARTO™ system, produced by Biosense Webster, Inc. (Diamond Bar, Calif.). In magnetic navigation systems, magnetic fields are typically generated by a location pad consisting of field generators. In such a system, magnetic position sensing may be used to determine position coordinates of the distal end of a tool inside a patient's organ. For this purpose, a driver circuit in a console or a location pad drives field generators to generate magnetic fields within the body of patient. Typically, the field generators comprise cords, which are placed beneath the patient's body at known positions external to the patient. These coils generate magnetic fields in a predefined working volume that contains the patient's organ to be explored. A magnetic field sensor within the distal end of the tool to be navigated generates electrical signals in response to these magnetic fields. A signal processor processes these signals in order to determine the position coordinates of the distal end, typically including both location and orientation coordinates. This method of position sensing is implemented in the above-mentioned CARTO™ system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

During a procedure using a particular tool, for example a catheter, with a magnetic navigation system, the location of the catheter's distal sensor is typically determined by measuring the main magnetic field enabled in the navigation system. In magnetic navigation systems used for navigating wireless tools, e.g., "wireless systems", there is a need to coordinate between the generator part, e.g., the coils, etc., and the receiver part, e.g., the sensors, etc. Typically, the charge of the magnetic field (positive or negative) in such wireless systems is determined as alternating current (AC). Certain materials have piezoelectricity, that is, the ability to generate an AC voltage and/or to vibrate when subjected to an AC voltage.

However, the piezoelectricity can cause a delay relative to transmission such that there is a need to determine the phase of the transmission. Ideally both generator and receiver would operate using the same clock but, due to physical or other constraints, two (or more) clocks must be used instead. Unfortunately, the use of more than one clock can result in skew between and/or among the clocks and can cause the wireless system to be not synchronized; that is, the different clocks have different times. A gong mechanism can be used to facilitate synchronization among the clocks. Typically, the gong mechanism re-sets or "zeros" all of the clocks by wirelessly transmitting a re-set or "zero" signal to all clocks. However, in some instances the wirelessly transmitted signal is lost and does not arrive at the clock to instruct the clock to re-set. In this situation, the clock(s) not receiving the signal are not re-set and thus lose synchronization with the other clock(s). Further, when more than one signal is lost at a particular clock, the lack of synchronization increases.

There is a need for a system and method that enables the clocks in the wireless system to be successfully synchronized and to remain synchronized with each other. An inventive "flywheel mechanism" to solve this need is presented.

FIG. 1 is a schematic overview of the system in accordance with an embodiment of the present invention. As shown in FIG. 1, the system may comprise a medical tool 10 (e.g., catheter, catheter tube, etc.), a work station 12 comprising at least a processor 14 having a clock 38 and a display or monitor 16, a catheter hub 18 having a clock 40, an LP driver 20, a patient (only head is shown) 22, WiFi antenna 24, RF Sync Tx antenna 26, RF Sync Rx antenna 28 and location pad 30. In one embodiment, the catheter hub 18 receives data from all of the sensors that are navigated, and the LP driver 20 drives current, such as AC, to the location pad 30, the current enabling the field generators to generate magnetic fields. In one embodiment, the catheter hub 18 comprises a WiFi antenna 24 and an RF Sync Rx antenna 28, for receiving signals from the tools that are navigated. In one embodiment, the LP driver 20 comprises a WiFi antenna 24 and an RF Sync Tx antenna 26 enabling the LP driver 20 to transmit current to the location pad 30.

The position and orientation of the distal end of the tool 10 may be ascertained by determining the position of the magnetic field locating sensor. The tool 10 may be locatable with a non-ionizing field, such as an electromagnetic or acoustic field. As discussed above, the tip of the tool 10 may comprise a transmitting or receiving antenna (not shown) for the relevant field. Receiving or transmitting antennas (not shown) for the non-ionizing field are attached to a patient to be examined. A receiver or transmitter is connected to these antennas, and converts the received field waves into electrical locating or image signals.

The location pad 30 may comprise coils (not shown), which are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The work station 12 can be detachably connected to the display 16. The work station 12 is also detachably connected to the catheter hub 18 to which one or more medical tools 10 can be connected. The connections may be hard-wired or WiFi connections, or both. The tool 10, such as a catheter or ENT tool, may be navigated through the patient's head 22. Although the work station 12, the LP driver 20 and the catheter hub 18 are shown as separate components, they may all be separate components, they may all be included together in a single component, or variously combined as fewer components.

FIG. 2 is a schematic overview of the "flywheel mechanism", which is an inventive method for synchronization of clocks within a wireless system. The method enables the clocks in the wireless system to continue to be synchronized even if a gong or re-set signal is lost at one (or more) clock(s). To overcome the problem caused by a lost or missing gong signal, the inventive technique comprises a learning technique and an inner estimator of the skew of the clock, thus enabling clock re-set even when a gong signal is not received. The following examples are used to illustrate, but not limit, the inventive technique.

In a first example a wireless system, such as the system shown in FIG. 1, comprises clock1 38 and clock2 40. Initially both clocks 38, 40 are set to "zero", or 12:00. After one hour, clock1 38 indicates 1:00 and clock2 indicates 1:05. When clock2 40 receives a gong signal, clock2 40 re-sets to 1:00 (to match, or synchronize with, clock1 38). Also, when the gong signal is received at clock2 40, this is reported to the processor 14 as data for learning the skew. After two hours, clock1 38 indicates 2:00, and clock2 40 indicates 2:05. Clock2 40 receives a gong signal and re-sets to 2:00; this data is also reported to the processor 14. This data indicates that clock2 40 is skewed five minutes behind clock1 38; that is, clock2 40 shows 1:05 when clock1 38 shows 1:00 (the difference between 1:05 and 1:00 is five minutes). Similarly, clock2 40 shows 2:05 when clock1 38 shows 2:00. Using at least this data, the processor 14 performs the inventive technique and "learns" that clock2 40 is skewed five minutes behind clock1 38. In one embodiment, the system learns the skew "on the fly"; that is, the system may use all gongs (gong signals) that were received and reported to the processor to build statistics (e.g., mean and standard deviation) and then use these statistics to estimate the missing gongs. As mentioned above, the statistics are collected from the catheter hub 18 by the processor 14 and analyzed for "learning".

After three hours, clock1 38 indicates 3:00, and clock2 40 indicates 3:05. At this point, no gong signal is received at clock2 40, so it does not re-set. However, in accordance with the "flywheel mechanism" methodology discloses herein, clock2 40 recognizes that a gong signal should have been received at 3:05 (because of the "learned" five minute skew) and thus clock2 40 is aware of a potential discrepancy. Since clock2 40 has "learned" of the five minutes per hour skew, clock2 40 can adjust accordingly. In this example, at about 3:10, when no gong signal is received, clock2 40 re-sets to 3:05 to correct for the five minute skew and the additional five minute wait for the gong signal, which should have been received at 3:05. Hence, when no gong signal is received, the estimated skew is used and the clock is re-set in accordance with this estimation. This estimated skew may be learned and may indicate a "typical delay" or skew. Regardless of whether or not the gong signal is received, learning the skew and then estimating the skew continues each time a gong signal is sent. In the example shown in FIG. 2, the gong signal is sent every hour but more or less time can elapse between sending of the gong signals. In one embodiment, learning or estimating the skew can be performed using Gaussian distribution fitting. This type of probability distribution fitting involves fitting a probability distribution, e.g., the distribution of the ideal or theoretical gong signal time, to a series of data, e.g., the repeated measurement of the gong signal data. This may enable the forecasting of the frequency of occurrence of the gong signal in a certain interval.

In a second example, clock1 38 and clock2 40 also start at 12:00. The gong signal is received at clock2 40 at 1:05 and clock2 40 is re-set to 1:00. The next gong signal is received at clock2 40 at 2:07 and the clock2 40 is re-set to 2:00. The flywheel mechanism learns that the average time lag or skew is six minutes (e.g., the average of five and seven minutes). By about 3:10, clock2 40 has not received a gong signal and the system recognizes that the gong signal should have been received at around 3:06. Hence, at 3:10, clock2 40 is re-set to 3:04 (subtracting the six minutes of average time lag and adjusting to the re-set time of four minutes after the average time lag e.g., 3:10-6 minutes. As with the first example, the learning continues so that each time a gong signal is received, the average time lag is adjusted incorporating the newly received time signal into the average time lag calculation. For ease of explanation, these examples use a one hour interval between gong signals. However, intervals of one or more milliseconds may also be used.

Figure 3:
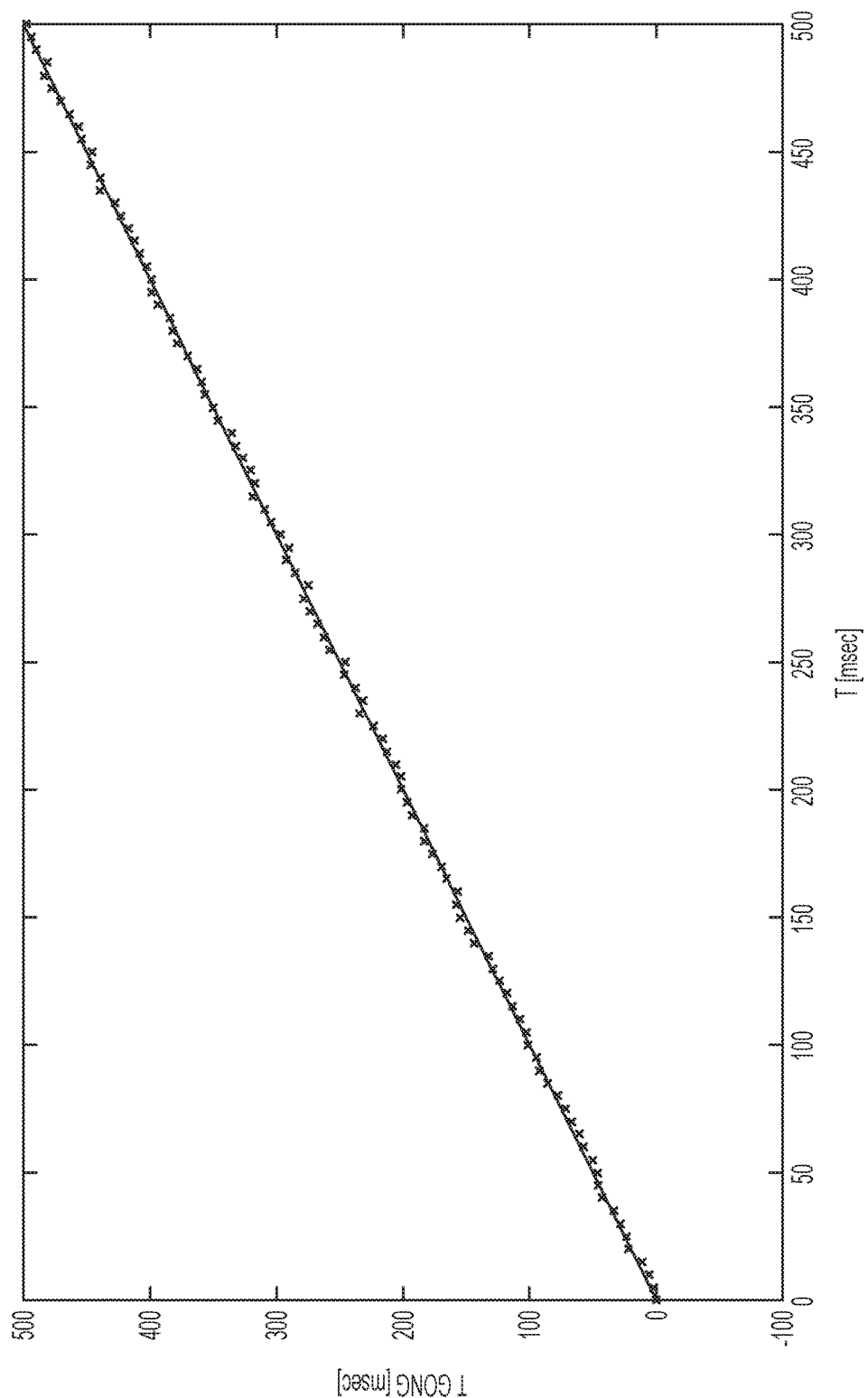
FIG. 3 is a graph comparing actual gong timestamp versus theoretical gong timestamp, in accordance with an embodiment of the present invention.

FIG. 3 is a graph illustrating the actual gong timestamp versus the theoretical gong timestamp. In the graph in FIG. 3, X is theoretical or expected gong timestamp and Y is actual timestamp of the received gong. If a system were perfect, (i.e. subject to no external interference), the actual timestamp would exactly match the theoretical timestamp, that is, y=x. However, since there indeed is interference in systems, the graph in FIG. 3 shows that there is some "jitter" around the theoretical values.

Figure 4:
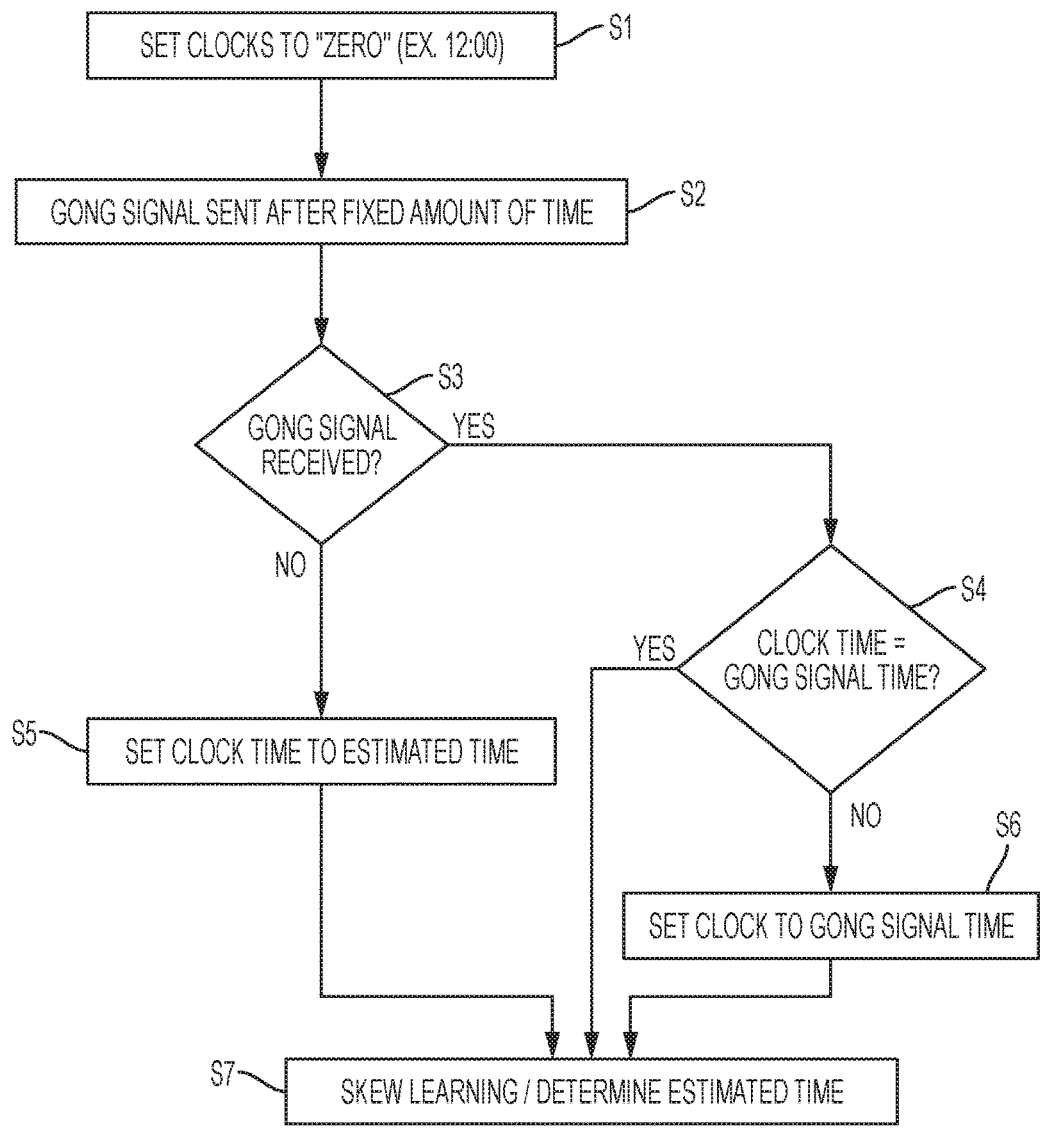
FIG. 4 is a flow diagram of the inventive method.

FIG. 4 is a flow diagram of the inventive method. In one embodiment, the method may proceed as follows. In step S1, the clocks are set to "zero" or 12:00. In step S2, a gong signal is sent to the catheter hub 18 after a fixed amount of time passes. In one embodiment, the fixed amount of time is sixty minutes (one hour).

If the gong signal is received at the clock (S3=YES), then determine whether the time on the clock equals the time sent by the gong signal. If the clock time is equal to the gong signal time (S4=YES), then proceed to step S7.

If the clock time does not equal the gong signal time (S4=NO), then at step S6 set the clock time is set to the gong signal time. In one embodiment, the difference between the gong signal time and the clock time is the determined, or "learned" skew or lag time. Proceed to step S7.

If the gong signal is not received at the clock (S3=NO), then the clock time is adjusted by the determined skew time to a time, e.g., estimated time, which estimates what the gong time would be if it were received.

At step S7, perform learning using the received gong signals and determine the estimated time. In one embodiment, performing learning at step S7 is done by determining the skew or lag time by calculating the average lag time as the average difference between the time on the clock and the time sent by the gong signal. For example, average lag time (ALT) equals the sum of the time on the clock (CT) minus time sent by the gong (GT) divided by the number of clock times (n), e.g., ALT=$\Sigma$(CT−GT)/n, where n is the number of clock times recorded. In Examples One and Two above, n=3 (1:00, 2:00, 3:00). More or fewer number of clock times are permitted. After completion of step S7, continue at step S2.

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements method described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for synchronization of a first clock and a second clock in a magnetic navigation system used for navigating a wireless tool, the method comprising:
    generating a magnetic field using the first clock;
    receiving, at the wireless tool, the magnetic field using the second clock,
    sending, over time, a plurality of gong signals at equal time intervals, each gong signal indicating a time of the first clock;
    determining whether each of the gong signals is received at the second clock;
    for each of the received gong signals:
        calculating a time difference between the time of the first clock and a time of the second clock;
        when the time of the first clock is not equal to the time of the second clock, setting the time of the second clock to the time of the first clock; and
        calculating a skew time between the first clock and the second clock based on the time differences calculated for each previously received gong signal; and
    when the gong signal is not received, adjusting the time of the second clock by the skew time.

2. The method according to claim 1, wherein calculating the skew time further comprises calculating an average of the time differences between the clock time of the second clock and the time of the first clock.

3. The method according to claim 1, wherein calculating the skew time further comprises calculating mean and standard deviation using the received gong signal, and the time of the second clock.

4. The method according to claim 1, wherein calculating the skew time further comprises using Gaussian distribution fitting.

5. The method according to claim 1, wherein the equal time intervals are one millisecond.

6. A system for synchronization of a first clock and a second clock in a magnetic navigation system used for navigating a wireless tool, the system comprising:
    a magnetic field generator configured to generate a magnetic field using the first clock;
    a wireless tool comprising one or more receivers configured to receive the magnetic field using the second clock;
    a processor, which is configured to:
        send, over time, a plurality of gong signals at equal time intervals, each gong signal indicating a time of the first clock;
        determine whether each of the gong signals is received at the second clock;
        for each of the received gong signals:
            calculate a time difference between the time of the first clock and a time of the second clock;
            when the time of the first clock is not equal to the time of the second clock, set the time of the second clock to the time of the first clock; and
            calculate a skew time between the first clock and the second clock based on the time differences calculated for each previously received gong signal; and
        when the gong signal is not received, adjust the time of the second clock by the skew time.

7. The system according to claim 6, wherein the processor is further configured to calculate the skew time by calculating an average of the time differences between the time of the second clock and the time of the first clock.

8. The system according to claim 6, wherein the processor is further configured to calculate the skew time by calculating mean and standard deviation using the received gong signal and the time of the second clock.

9. The system according to claim 6, wherein the processor is further configured to calculate the skew time using Gaussian distribution fitting.

10. The system according to claim 6, wherein the equal time intervals are one millisecond.

11. A non-transitory computer readable storage medium in which computer program instructions are stored, which instructions, when executed by a computer, cause the computer to perform a method for synchronization of a first clock and a second clock in a magnetic navigation system used for navigating a wireless tool, comprising:
   generating a magnetic field using the first clock;
   receiving, at the wireless tool, the magnetic field using the second clock,
   sending, over time, a plurality of gong signals at equal time intervals, each gong signal indicating a time of the first clock;
   determining whether each of the gong signals is received at the second clock;
   for each of the received gong signals:
      calculating a time difference between the time of the first clock and a time of the second clock;
      when the time of the first clock is not equal to the time of the second clock, setting the time of the second clock to the time of the first clock; and
      calculating a skew time between the first clock and the second clock based on the time differences calculated for each previously received gong signal; and
   when the gong signal is not received, adjusting the time of the second clock by the skew time.

12. The computer readable storage medium according to claim 11, wherein calculating the skew time further comprises calculating an average of the time differences between the time of the second clock and the time of the first clock.

13. The computer readable storage medium according to claim 11, wherein calculating the skew time further comprises calculating mean and standard deviation using the received gong signal, and the time of the second clock.

14. The computer readable storage medium according to claim 11, wherein calculating the skew time further comprises using Gaussian distribution fitting.

15. The computer readable storage medium according to claim 11, wherein the equal time intervals are one millisecond.

16. The method according to claim 1, further comprising:
   determining a next time for the second clock to receive a next gong signal based on the skew time; and
   when the gong signal is not received, adjust the time of the second clock after an amount of time has expired after the determined next time.

\* \* \* \* \*

UNITED STATES PATENT AND TRADEMARK OFFICE
CERTIFICATE OF CORRECTION

PATENT NO. : 10,514,719 B2
APPLICATION NO. : 15/634220
DATED : December 24, 2019
INVENTOR(S) : Assaf Govari et al.

It is certified that error appears in the above-identified patent and that said Letters Patent is hereby corrected as shown below:

On the Title Page
After Item (72), in Column 1, insert -- (73) Assignee: Biosense Webster (Israel) Ltd., Yokneam (IL) --, therefor.

In the Specification
In Column 1, Line 16, delete "to to" and insert -- to --, therefor.
In Column 2, Line 11, delete "cords," and insert -- coils, --, therefor.

In the Claims
In Column 6, Line 10, in Claim 1, delete "clock," and insert -- clock; --, therefor.
In Column 6, Line 29, in Claim 2, delete "clock time" and insert -- time --, therefor.
In Column 7, Line 21, in Claim 11, delete "clock," and insert -- clock; --, therefor.

Signed and Sealed this
Twenty-fourth Day of October, 2023

Katherine Kelly Vidal
*Director of the United States Patent and Trademark Office*